United States Patent [19]

Beland

[11] Patent Number: 5,473,088
[45] Date of Patent: Dec. 5, 1995

[54] DIRECT NEUTRALIZATION OF N-ACYL SARCOSINES

[75] Inventor: John M. Beland, Bedford, N.H.

[73] Assignee: Hampshire Chemical Corp., Lexington, Mass.

[21] Appl. No.: 255,186

[22] Filed: Jun. 7, 1994

[51] Int. Cl.⁶ .................................................. C07C 231/24
[52] U.S. Cl. .............................. 554/70; 554/68; 554/195; 554/63
[58] Field of Search .................................. 554/63, 68, 70, 554/195; 282/127

[56] References Cited

U.S. PATENT DOCUMENTS

| | | | |
|---|---|---|---|
| 3,450,752 | 6/1969 | Inklaar | 260/534 |
| 3,836,551 | 9/1974 | Schroeder et al. | 260/404 |
| 4,436,910 | 3/1984 | Kleemann et al. | 546/245 |
| 5,328,629 | 7/1994 | Crudden | 252/117 |

FOREIGN PATENT DOCUMENTS 1486988  3/1967  France.

*Primary Examiner*—José G. Dees
*Assistant Examiner*—Deborah D. Carr
*Attorney, Agent, or Firm*—Nields & Lemack

[57] ABSTRACT

A process for the direct neutralization of N-acyl sarcosines wherein all raw materials and products are in the liquid state up to the final crystallization of the product. The N-acyl sarcosines are neutralized in a continuous or batch mode with caustic such as aqueous hydroxide at elevated temperatures to produce a molten, free flowing liquid, which can then be crystallized to solid product.

10 Claims, No Drawings

DIRECT NEUTRALIZATION OF N-ACYL SARCOSINES

BACKGROUND OF THE INVENTION

The use of sarcosinate surfactants, and in particular, N-acyl sarcosinates in the manufacture of soaps is well known. Typically, the sarcosinate is used in the form of its sodium, potassium, triethanolamine or ammonium salt solution. N-acyl sarcosinates are produced commercially by the Schotten-Baumann reaction of the sodium salt of sarcosine with the appropriate fatty acid chloride under carefully controlled conditions:

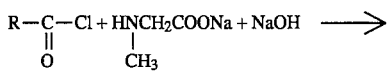

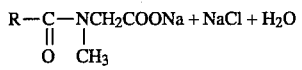

where R is typically a fatty acid of chain length $C_{10}$ to $C_{18}$, commonly made from lauric, coconut, palmitic, myristic, steric or oleic acid. After the reaction is complete, the crude sodium salt solution is acidified to liberate the free fatty sarcosine acid which is separated from the aqueous by-products. It then is neutralized to a salt form. Sarcosinates such as sodium lauroyl sarcosinate, sodium cocoyl sarcosinate and sodium myristoyl sarcosinate are commercially available under the trademark HAMPOSYL® from Hampshire Chemical Corp., as 30% active solutions in water. To produce soap bars, most of the water must be removed, which may require heating the mixture to temperatures as high as about 150° C. More concentrated sarcosinate solutions are difficult to produce because of high viscosity and low solubility. Indeed, sarcosinate salt solutions of products with a chain length of greater than $C_{14}$ are not produced because lower solubility would require an even more dilute solution. Furthermore, as the pH of the N-Acyl sarcosine is raised from pH 2 towards pH 5, gel phases of high viscosity are often encountered (particularly with myristoyl, steroyl and oleoyl sarcosines), which make production of a uniform and homogeneous product difficult and time consuming. As a result, when a product of nearly 100% activity is required, the 30% sarcosinate solution must be spray dried, which is a difficult and costly process. In addition, the spray dried product is a dusty and talc like material that is difficult to handle.

SUMMARY OF TEE INVENTION

The problems of the prior art have been overcome by the instant invention, which provides a process for the direct neutralization of N-acyl sarcosines wherein all raw materials and products are in the liquid state up to the final crystallization of the product. In general terms, the instant process involves neutralization of N-acyl sarcosines with aqueous concentrated caustic, preferably alkali metal hydroxide or an amine such as triethanolamine, to produce a free flowing liquid. By operating at elevated temperatures, water formed from the neutralization plus the water present in the caustic is flashed off from the solution. The process can be run continuously or as a batch process. The resulting solution then can be crystallized such as with a spray crystallizer into a dry, free flowing form.

DETAILED DESCRIPTION OF THE INVENTION

Suitable N-acyl sarcosines for the present invention include lauroyl sarcosine, cocoyl sarcosine, palm-kernel sarcosine, myristoyl sarcosine, palmitoyl sarcosine, stearoyl sarcosine and oleoyl sarcosine.

The pure N-acyl sarcosine can be easily neutralized using a caustic, preferably an alkali metal hydroxide or an amine, most preferably sodium hydroxide or potassium hydroxide, as 50% or 45% solutions. The neutralization can be conducted at atmospheric pressure and at temperatures above the melting point of the product, preferably above about 130° C., more preferably above about 140° C. in order to flash off the water formed by the neutralization and introduced by the caustic. In this embodiment, if the residence time during neutralization is kept to a minimum, product decomposition is also minimized, and the free fatty acid and the color of the product are not significantly increased. It is believed that the rapid removal of water minimizes the hydrolysis reaction back to the free fatty acid. Preferably the reaction is conducted in an inert atmosphere, such as under an inert gas sparge of nitrogen, to reduce oxidation and minimize color formation that might otherwise occur at the elevated temperatures used for neutralization. Free fatty acid levels under about five percent, preferably under about four percent, APHA colors of less than about 100, and water levels less than about five percent, preferably less than about three percent, are desired and can be achieved with the instant invention.

Alternatively, the neutralization can be carried out below the melting point of the product (70°–100° C., more preferably 80°–100° C.) and at reduced pressure. Using such conditions, residence times of even one hour have been found to be not detrimental to the product. Preferably, a reduced pressure of at least 20 inches Hg, more preferably greater than 25 inches of Hg, and a residence time of less than one hour is used. The lower the pressure, the faster the water is removed, and less decomposition (hydrolysis) results. The product is a liquid at about 70° to 100° C. when water is present, and the product crystallizes as the water is removed. The key is that even though the temperature is below the melting point, the reactants are in the liquid state long enough to provide sufficient mixing to make a homogenous mixture. In this embodiment, it is preferable that the steps of reaction, mixing, drying and crystallizing all be carried out in the same processing equipment.

Sufficient base is added to the sarcosine so that the pH of the solution is maintained in the range of about 5.5 to about 8.5. Since the reactants are in the liquid form, pH is relatively easy to adjust and maintain. When the pH is above 6.5, the product begins to foam more vigorously, and a large reaction vessel may be required to accommodate the foam.

Formation of free fatty acid, free sarcosine, and color are also minimized by reducing the time that the product is exposed to the elevated temperatures. Residence time can be minimized by conducting the process in a continuous mode rather than batch. Preferred residence times are from about 20 to about 30 minutes, more preferably 20 minutes or less, at temperatures of from about 130° to 155° C. and pH of 5.5 to 8.5 at atmospheric pressure.

Crystallization of the resulting product can be accomplished by any suitable means. For example, the molten product can be spray crystallized with apparatus similar to spray dryers, except that cooling air is used. By appropriately atomizing the product such as by directing it through a small orifice with the application of high pressure, and by blowing cooled air into the spray crystallizer chamber, sufficient cooling takes place to cause crystallization into a dry, free-flowing form that is less dusty than product made by conventional means. Where the neutralization is carried out at reduced pressure, the product can be crystallized by evaporative cooling.

The instant invention will be better understood by referring to the following specific but non-limiting examples. It is understood that said invention is not limited by these procedures which are offered merely as illustrations; it is also understood that modifications can be made without departing from the spirit and scope of the invention.

EXAMPLES 1–3

A continuously feeding apparatus was constructed utilizing a 1 liter bottom draining resin kettle; an overhead agitator with a steel shaft having two propeller-type blades low on the shaft; a heating mantle; a sparge tube for inert gas feed; two dropping funnels; and a thermocouple connected to a heating control for the heating mantle.

Three runs were made using this apparatus. Run number 1 used lauroyl sarcosine in the form of the wet acid (14% water), and 50% sodium hydroxide. Run number 2 used the dry acid (less than about 1% water) and 50% sodium hydroxide, and the above apparatus was modified by replacing the dropping funnels with Masterflex pumps to feed the raw materials at a more even rate, and a cover was added to the resin kettle with a tube connected to an aspirator to draw off the water vapor. Run number 3 was the same as run number 2, except that the wet acid used in Run number 1 was used.

In all three runs, the reactor was charged with about 400 mls of acid and heated to 135° C. A continuous sparge of nitrogen was started as soon as there was liquid in the reactor. At 135°, the feed of 50% sodium hydroxide was started and the acid feed was adjusted so the combination of the two would be about 20 mls/min. with the pH maintained at 5.5 to 7.5. The bottom drain was then adjusted to maintain about 400 mls. in the reactor. The residence time in the reactor was 20 minutes. The heating was adjusted so as to maintain the temperature at 135° to 150° C. Two samples were taken from each run. The first was taken when the reaction reached equilibrium and the second was taken when the reaction had been running for at least 0.5 hours. The samples were allowed to crystallize overnight in trays. They were then ground to a powder and analyzed.

The results are shown in Table 1 below.

TABLE 1

| RUN NO. | % ACTIVE INGRED. | % WATER | 10% pH | 20% COLOR | % FREE FATTY ACID |
|---|---|---|---|---|---|
| 1A | 96.3 | 3.2 | 7.5 | 92 | 3.9 |
| 1B | 97.7 | 2.6 | 7.8 | 82 | 5.4 |
| 2A | 94.3 | 2.2 | 6.8 | 112 | 3.2 |
| 2B | 82.2 | 3.2 | 6.0 | 28 | 2.7 |
| 3A | 91.3 | 3.0 | 6.5 | 87 | 3.9 |
| 3B | 94.0 | 4.8 | 6.8 | 83 | 3.7 |

EXAMPLES 4–10

A series of batch tests were run in equipment capable of carrying out the reaction, mixing, drying and crystallizing steps, available from LIST, Inc. as DTB-3 mixer/dryer. The apparatus was heated by hot oil (Califlo HTF) at temperatures ranging from 73 to 118° C. Condensate was recovered with a chilled water cooled condenser. The unit was powered with a hydraulic drive (7.5 kw) and the agitator rpm was adjustable between 0 and 70. Power uptake was indicated by hydraulic pressure and the bed temperature was indicated by a J-type thermocouple located in one of the hooks.

Lauroyl sarcosine (available commercially from Hampshire Chemical Corp. as HAMPOSYL L® surfactant) was poured into the heated unit. The total charge was 2570 g for the first five (5) trials and 3158 g for the last trial which represents a fill level of about 40%. A 50% sodium hydroxide solution was metered into the system at a rate of 40 g/min over the first 15 to 20 minutes, such that the caustic charge was roughly 693–733 g. The reaction was visually monitored and the appearance of foam and dry solids noted during trial. The unit was sampled for pH and moisture content after the foaming subsided and a free-flowing powder was observed.

The results are summarized in Table 2.

As shown in Table 2, the jacket temperature was varied between 73° and 118° C. Agitator speed was maintained at either 30 or 44 rpm. The reaction was run under atmospheric conditions, under vacuum, and under vacuum/with nitrogen sweep. All trials resulted in the generation of dry free flowing solids. Final moisture content varied between 2.8 and 6.8% (less than 5% is desired), and the pH varied between 6.6 and 7.5.

TABLE 2

| Trial No. | Jacket Temp. (°C.) | Reactor Press. | Reactor Charge (g) | NaOH Charge (g) | Mixing Speed | Hydraulic Press. | Final Moist. | Final pH | Run Time (min.) |
|---|---|---|---|---|---|---|---|---|---|
| 1 | 118 | ATM | 2570 | 709 | 30 | 0 | 4.7 | 7.3 | 75 |
| 2 | 118 | 10 in. Hg | 2570 | 727 | 30 | 0 | 6.8 | 7.5 | 105 |
| 3 | 118 | 15 in. Hg/N$_2$ sweep | 2570 | 720 | 30 | 0 | 3.5 | 7.4 | 41 |
| 4 | 81 | 20 in. Hg/N$_2$ sweep | 2570 | 704 | 30 | 0 | 2.87 | 7.4 | 44 |
| 5 | 73 | 20 in. Hg/N$_2$ sweep | 2570 | 693 | 44 | 0 | 5.87 | 6.9 | 27 |
| 6 | 73 | 20 in. Hg/N$_2$ | 3158 | 733 | 44 | 0 | 5.78 | 6.6 | 52 |

TABLE 2-continued

| Trial No. | Jacket Temp. (°C.) | Reactor Press. | Reactor Charge (g) | NaOH Charge (g) | Mixing Speed | Hydraulic Press. | Final Moist. | Final pH | Run Time (min.) |
|---|---|---|---|---|---|---|---|---|---|
| | | sweep | | | | | | | |

What is claimed is:

1. A process for the neutralization of N-acyl sarcosine, consisting essentially of reacting said sarcosine with caustic at a temperature higher than the melting point of said sarcosine, and crystallizing the resulting neutralized product.

2. The process of claim 1, wherein said caustic is selected from the group consisting of alkali metal hydroxide and triethanolamine.

3. The process of claim 1, wherein said caustic is a 50% solution of sodium hydroxide.

4. The process of claim 1, wherein said N-acyl sarcosine is lauroyl sarcosine.

5. The process of claim 1 wherein the pH of the reaction solution is maintained at about 5.5 to 8.5.

6. The process of claim 1 wherein the residence time of the reactants in the reactor is from about 20 to about 30 minutes.

7. The process of claim 1 wherein the reaction temperature is from about 130° to about 140° C.

8. The process of claim 1, wherein said temperature is sufficiently high to flash off water from the solution consisting essentially of said sarcosine and said caustic.

9. A process for the neutralization of N-acyl sarcosine, consisting essentially of reacting said sarcosine with caustic at a temperature of about 70°–100° C. and at a reduced pressure of at least 20 inches Hg.

10. The process of claim 8 wherein said reaction is carried out at a pH of from about 5.5–8.5.

* * * * *